United States Patent
Fujii et al.

(10) Patent No.: US 7,356,176 B2
(45) Date of Patent: Apr. 8, 2008

(54) MOUNTING-ERROR INSPECTING METHOD AND SUBSTRATE INSPECTING APPARATUS USING THE METHOD

(75) Inventors: Yoshiki Fujii, Fukuchiyama (JP); Hiroshi Yamazaki, Kyoto (JP)

(73) Assignee: Omron Corporation, Kyoto-Shi (JP)

( * ) Notice: Subject to any disclaimer, the term of this patent is extended or adjusted under 35 U.S.C. 154(b) by 834 days.

(21) Appl. No.: 10/786,605

(22) Filed: Feb. 26, 2004

(65) Prior Publication Data

US 2005/0190956 A1   Sep. 1, 2005

(51) Int. Cl.
*G06K 9/00* (2006.01)
(52) U.S. Cl. .............. 382/141; 250/559.44; 356/237.2; 382/190
(58) Field of Classification Search .................. 29/832, 29/833; 382/141, 145, 149, 151, 190; 250/559.44; 356/237.2
See application file for complete search history.

(56) References Cited

U.S. PATENT DOCUMENTS

| | | | |
|---|---|---|---|
| 4,787,143 A | 11/1988 | Yagi et al. | |
| 6,480,751 B1 | 11/2002 | Kuribayashi et al. | |
| 6,573,523 B1 * | 6/2003 | Long | 250/559.4 |
| 7,054,705 B2 * | 5/2006 | Ogawa et al. | 700/121 |
| 7,114,249 B2 * | 10/2006 | Murakami | 29/833 |
| 2003/0169418 A1 * | 9/2003 | Fujii et al. | 356/237.2 |
| 2004/0076323 A1 * | 4/2004 | Fujii et al. | 382/151 |
| 2005/0190956 A1 * | 9/2005 | Fujii et al. | 382/141 |

FOREIGN PATENT DOCUMENTS

| | | |
|---|---|---|
| CN | 86104342 | 6/1987 |
| CN | 1133359 | 12/2003 |
| EP | 1 388 738 A1 | 2/2004 |
| JP | 7-30288 | 1/1995 |
| JP | 2002-181731 A | 6/2002 |
| JP | 2002-183712 A | 6/2002 |

\* cited by examiner

*Primary Examiner*—Gregory M Desire
(74) *Attorney, Agent, or Firm*—Foley & Lardner LLP

(57) ABSTRACT

When a component is replaced or replenished in a predetermined feeder, mounters 3A and 3B refer to mount data in accordance with the feeder number for the feeder and read out the mounting position of the replaced or replenished component. The mounting position data is transmitted to a substrate inspecting apparatus 5 together with the substrate identification code of a substrate first processed after reel replacement. When the substrate corresponding to the substrate identification code is supplied, the substrate inspecting apparatus 5 refers to substrate inspection data in accordance with the mounting position data, specifies a component to be inspected, and executes the mounting error inspection according to character-string recognition for the specified component. When a mounting error is detected in this inspection, the substrate inspecting apparatus 5 transmits no-good determination to the mounters 3A and 3B receiving information.

11 Claims, 10 Drawing Sheets

MOUNTING-ERROR INSPECTING METHOD AND SUBSTRATE INSPECTING APPARATUS USING THE METHOD

BACKGROUND OF THE INVENTION

1. Field of the Invention

The present invention belongs to a technical field for inspecting a printed circuit board (hereafter referred to as "component mounting substrate" or simply referred to as "substrate") with components mounted. Particularly, the present invention relates to a method for performing inspection on whether a correct component is mounted on a substrate to be inspected and an apparatus having a function of executing the inspecting method.

2. Description of Prior Art

A component mounting machine referred to as "mounter" has been used so far in order to automate high-density component mounting. A plurality of component supplying devices respectively referred to as "feeder" is set on the mounter. Each feeder holds many same types of components and is managed in accordance with a specific identification number referred to as "feeder number".

Data showing that the component of which feeder is mounted on which substrate (generally referred to as "mount data") is previously entered in the controlling section of the mounter. The mount data is generated in accordance with CAD data for designing a substrate, in which data values including the mounting position, height, and feeder number of a feeder serving as a component supplying source are set for each component. The controlling section controls a head portion for mounting a component in accordance with the mount data and takes out a component from a feeder corresponding to each mounting position and then, sets the component to a corresponding mounting position.

A tape feeder widely used for this type of mounter uses a reel on which a tape housing many components is wound. The reel is removal. When a tape runs out, an old reel is properly replaced with a new reel. Moreover, when a component to be mounted is changed in accordance with the change of a substrate to be fabricated, the reel is replaced with a reel for housing the changed component.

Thus, a component mounting machine makes it possible to automatically mount a component adapted for the mounting position of each component in accordance with mount data. However, processing of replenishing component to a feeder or replacing components in the feeder in accordance with the change of substrate to be fabricated is performed by man power. Therefore, when a person in charge supplies an incorrect component, it is impossible to supply a correct component to subsequent substrate and thus, a defective substrate is produced.

To detect a component mounting error due to the above human error, inspection for determining whether each component is a correct component is conventionally executed in a substrate inspecting apparatus for inspecting a component mounted state (in this specification, the above inspection is referred to as "mounting error inspection"). The mounting error inspection determines whether a character string in an image obtained by imaging a component by a video camera coincides with a previously enter correct character string by noticing that a character string showing the type of a component or the like is printed on the body of the component. Specifically, a method of performing pattern matching between the above image and the image of a correct character string and a method of applying character recognition to the image and collating the recognized character string with an entered character string are executed.

However, because these methods respectively requires a lot of time for processing, when executing inspection for each component on every substrate, a large amount of time is necessary for the inspection.

Moreover, this type of determination processing is easily influenced by a very small foreign matter, character bleeding, chip, or change of font. Therefore, even when a character string is proper, it may be determined that the character string is improper. Therefore, the so-called disinformation occurs that no-good determination is output in spite of a good component and moreover, a problem occurs that the accuracy and efficiency of the inspection are extremely deteriorated.

Japanese Patent Laid-Open Publication No. 2002-183712 is present as the prior art for decreasing the number of erroneous recognitions. In the case of this patent document, when comparing a character string extracted from the image of a component with an expected character string to be recognized, it is recognized that a character string is proper when the number of characters obtained through coincidence determination in the character string becomes a predetermine number or more.

However, even by using the method disclosed in Japanese Patent Laid-Open Publication No. 2002-183712, when a component whose character string is easily erroneously recognized is included in components, it is difficult to lower the frequency at which disinformation occurs.

SUMMARY OF THE INVENTION

The present invention is made to solve the above problems and its object is to improve the efficiency and accuracy of inspection by restricting substrates and components to which mounting error inspection is applied.

As described above, a component mounting error occurs due to a human error in a component mounting step. Therefore, when a component is replenished or replaced due to the change of a substrate to be fabricated in the component mounting step, a mounting error may occur in the component to be replenished or replaced.

In this case, if it is possible to specify a substrate first fabricated after the above operation, it is possible to consider that components of subsequent substrates are correct unless a mounting error occurs in the specified substrate. Moreover, even if it is impossible to specify a substrate, it is possible to check whether a mounting error occurs in substrates after the above operation by continuing inspection until a substrate immediately after the above operation securely arrives.

However, when no mounting error occurs in a substrate before the above operation, it is possible to consider that it is unnecessary to execute inspection for a clearly correct component by determining whether the replace or replenished component is a correct component.

The present invention greatly improves the efficiency of mounting error inspection and reduce the number of pieces of disinformation in accordance with the above consideration. In the case of a first mounting-error inspecting method of the present invention, when processing of replacing or replenishing a component is performed in a component mounting step, component identifying information for identifying the component and substrate identifying information for identifying a specific substrate on which the component is mounted are set, the component identifying information and substrate identifying information set in the component mounting step are obtained, and a substrate corresponding to the substrate identifying information is specified among supplied substrates to execute inspection on whether a correct component is mounted on the specified substrate. Moreover, in the case of the above inspection, the following steps are executed: a step of specifying a component to be inspected in accordance with the component identifying information, a step of obtaining the image of the component to be inspected and extracting a character string from the image, and a step of comparing the extracted character string with a character string to be printed on the component to be inspected and thereby determining whether the component to be inspected is a correct component.

In this case, the component mounting step corresponds to a step executed by the above mounter and the inspecting step corresponds to a step executed by a substrate mounting apparatus. Though it is preferable to set a substrate carrying conveyer between these apparatuses, it is not always necessary to set the conveyer between them. Moreover, it is allowed to execute a soldering step before executing the component mounting step and inspecting step.

Replacement of components represents that a component held by a predetermined feeder is removed and other component is supplied when the component to be manufactured is changed. Replenishment of a component represents that the same component is replenished to a predetermined feeder when a component runs out from the feeder. In the case of the above tape feeder, the replacement and replenishment are performed by replacing reels. However, it is possible to use not only a tape feeder but also a tray feeder or stick feeder.

The component identifying information of two pieces of identifying information set in the component mounting step can be used as feeder identifying information (the above described feeder number) when the mounting position of or type of a component to be replaced or replenished or the component is supplied. The component identifying information can be fetched from the above mount data. For example, when a component is replaced or replenished, it is possible to obtain the feeder number of the feeder relating to the component and use the component mounting position corresponding to the number as component identifying information. Moreover, when a component type is included in the mount data, it is possible to use the component type corresponding to the feeder number as component identifying information. Furthermore, when mount data is also prepared in an inspecting step, it is allowed to use a feeder number as component identifying information.

However, the substrate identifying information is information individually assigned to each substrate. Therefore, it is preferable to set the information in accordance with information which can be easily confirmed by an actual substrate. For example, it is possible to read identifying information recorded in a substrate to be first processed when a component mounting step is temporarily stopped to replace a reel and then restarted and use the information as substrate identifying information by recording recognizable information in the substrate in accordance with an optical mark recognition (OMR) technique such as attaching a bar code label showing identifying information and printing a numeral string according to a specific font.

It is preferable to set a reader dedicated to read processing to a component mounting machine. It is preferable to automatically operate the machine when supply of components of a feeder is completed. However, it is also allowed to operate the machine through operations of a person in charge.

Moreover, it is preferable to use information read from a first substrate using a replaced or replenished component as substrate identifying information. However, it is also allowed to use information read from a second substrate or a substrate after the second substrate to be processed. Furthermore, it is allowed to set a plurality of pieces of substrate identifying information by reading a plurality of substrates.

In an inspecting step, it is possible to successively capture prepared substrates and inspect them in accordance with image processing. In the inspecting step, it is preferable to be able to obtain the substrate identifying information and component identifying information at an optional timing. However, the inspecting step is not restricted to the above mentioned. For example, when other device (such as soldering device) is set between a mounter and a substrate inspecting apparatus or devices are not connected by a conveyer, it is allowed to store the identifying information recognized by the mounter in a predetermined storing medium and set the storing medium to a substrate inspecting apparatus so as to read out each piece of information.

In the case of inspection according to the above method, only a replaced or replenished component is inspected for a specific substrate on which the component is mounted in a component mounting step. For this inspection, it is preferable to previously individually enter a character string to be compared for each component to be mounted (character string to be printed on a component to be inspected). However, the inspection is not restricted to the above mentioned. Moreover, when information including positional information and type of component is entered as inspection data for each component, it is allowed to separately enter a character string to be printed on the component for each type of component and fetch a character string corresponding to component identifying information out of the entered character strings.

According to the above method, because a substrate or component to be inspected is specified, it is possible to greatly decrease the time required for inspection. Moreover, because only a component in which a mounting error may occur is inspected, a "mounting error" is not determined on other clearly correct components and therefore, it is possible to greatly reduce the number of pieces of disinformation.

Moreover, because a plurality of same components is generally mounted on a substrate, it is preferable to successively position an imaging device on components to be inspected to image the components in the case of processing of obtaining the image of a component to be inspected in the case of the above inspection. However, obtainment of an image is not restricted to the above mentioned. It is also possible to use processing of imaging the whole or a part of a substrate, and extracting and cutting off an image region including a component to be inspected from an obtained image.

Moreover, in the case of the above method, it is allowed to apply mounting error inspection only to one substrate specified in accordance with substrate identifying information. However, without being restricted to the above method, it is preferable to execute the same inspection for a predetermined number of substrates supplied after a substrate specified as a substrate corresponding to substrate identifying information. This is because an erroneous recognition easily occurs in the recognition processing for a character string and when the number of substrates to be inspected is restricted to one, it is impossible to ensure a sufficient recognition accuracy for the component to be inspected as described above. Moreover, by executing the above mentioned, it is possible to prevent erroneous determination when substrate identifying information is erroneously set in a component mounting step and the identifying information on a substrate before using a replaced or replenished substrate is set.

Moreover, to execute mounting error inspection for a plurality of substrates, it is possible to optionally set the number of substrates to be inspected in accordance with the recognition accuracy of an actual character string. However, when considering all substrates fabricated in a component mounting step, it is possible to greatly decrease the number of substrates to be inspected.

Then, in the case of a second inspecting method of the present invention, when processing of replacing or replenishing a component is executed in a component mounting step, the component identifying information for identifying the component is set. Moreover, in an inspecting step, the component identifying information set in the component mounting step is obtained, a step of specifying a component to be inspected in accordance with the component identifying information is executed, and then inspection on whether a correct component is mounted is executed for a predetermined number of substrates supplied after obtaining the component identifying information. In the case of this inspection, the following steps are executed: a step of obtaining images of the components to be inspected and extracting character strings from the images and a step of determining whether the components to be inspected are correct components by comparing the extracted character stings with character strings to be printed on the components to be inspected.

In the above case, processing of recognizing component identifying information in the component mounting step and processing of obtaining component identifying information in the inspecting step can be executed similarly to the case of the first method. Moreover, steps to be executed for inspection can be performed similarly to the case of the first method.

The above second method can be applied to a case in which substrate identifying information cannot be set. The number of substrates to be inspected in this method corresponds to the maximum number of substrates which can be set between a component mounting step and an inspecting step. Preferably, it is recommended to use a number obtained by adding a predetermined weight to the maximum number of substrates. Moreover, it is preferable to obtain each piece of identifying information in the inspecting step through communication. For example, it is preferable to set a conveyer for carrying substrates between a mounter and a substrate inspecting apparatus, connect the mounter with the apparatus on-line, and quickly carry the substrates passing through the component mounting step to the inspecting step so that the set component identifying information can be transmitted to the inspecting step.

Thus, when a component is replaced or replenished, it is possible to execute inspection until a substrate with the component mounted securely passes and conform whether the replaced or replenished component is proper. Moreover, also in this method, only replaced or replenished substrates are inspected, other clearly correct components are not erroneously determined and thus, it is possible to greatly reduce the number of pieces of disinformation.

Then, modes applied to the first and second inspecting method in common is described below.

In the case of the first mode, component identifying information is information showing the mounting position of the component to be replaced or replenished on a substrate and in a step of specifying the components to be inspected and substrate design data or substrate inspection data for a substrate to be inspected are referred in accordance with the mounting position so as to specify a component to be inspected.

In the above case, it is possible to obtain the information showing the mounting position from the above mount data.

The substrate design data is data generated by a substrate designing CAD system, which can include various deign data values for fabricating a substrate such as design data for layers (plastic potion and copper foil portion) of a substrate, solder-cream printing mask data, and the position, type (type of component), and shape of each mounted component.

Substrate inspection data is obtained by integrating inspection data set for each component on a substrate to be inspected (referred to as "component inspection data" in the case of this specification). It is possible to include an inspection-region setting position, various parameters for inspection (such as binary threshold values for extracting color patterns), and a criterion of a corresponding component in each component inspection data.

To generate substrate inspection data and the above mount data, it is possible to use the substrate design data. For example, it is possible to efficiently generate the substrate inspection data by previously setting and entering the information necessary to execute specific inspection every type of component and applying entered information adapted for each component to the mounting position of each component shown by the substrate design data.

According to the above mode, a step of specifying a component to be inspected makes it possible to accurately extract a component corresponding to a mounting position shown by component identifying information and specify the component as a component to be inspected.

Moreover, in the case of another mode, component identifying information is information showing the type of the component to be replaced or replenished and the above step of specifying a component to be inspected specifies a component to be inspected by referring to substrate design data or substrate inspection data for a substrate to be inspected in accordance with the above type of component.

It is possible to use not only a manufacturing type of a component manufacturer but also a component symbol decided by a user to order the component for a type of component. It is also possible to recognize the type of component in accordance with the above mount data.

The above mode makes it possible to accurately specify a component to be inspected by extracting a component corresponding to the type of component shown by component identifying information from substrate design data or substrate inspection data.

Because control based on substrate inspection data is usually performed in an inspecting step, it is preferable to use substrate inspection data as the data to be referred in accordance with the above mounting position.

However, a type of component may not be included in substrate inspection data. In this case, it is necessary to specify a component to be inspected by using substrate design data. In this case, however, when there is a plurality of same types of components, it is possible to express component identifying information by one type of component. Therefore, it is possible to decrease the time required for transceiving particularly when transmitting component identifying information to a substrate inspecting apparatus compared to a case of transmitting mounting position data.

Moreover, in the case of another mode, component identifying information is identifying information for a feeder to which the component to be replaced or replenished is supplied and a step of specifying the component to be inspected specifies a component to be inspected by referring to the mount data used in the component mounting step in accordance with the identifying information.

To execute the mode, it is necessary to previously introduce mount data same as that used for a component mounting machine into an inspecting apparatus. It is possible to transmit the mount data from a component mounting machine. Moreover, it is possible to transmit the mount data by a method of reading mount data stored in a storing medium.

According to the above mode, it is possible to specify a component to be inspected by extracting the mounting position data corresponding to the feeder identifying information shown by component identifying information from mount data in an inspecting step. Also in this case, it is possible to express a plurality of same type of components to be inspected by one piece of component identifying information. Therefore, it is possible to decrease the processing time for transmitting component identifying information to a substrate inspecting apparatus. Moreover, according to the above mode, it is possible to simplify the processing for setting component identifying information because it is only necessary to recognize a feeder to which components are actually supplied without referring to mount data in a component mounting step.

In the case of still another preferable mode, when it is determined that a predetermined number of components among a plurality of components specified as those to be inspected are correct components, an inspection result is output that correct components are mounted on a substrate to be inspected. This mode premises that a plurality of same components is normally mounted on a substrate and a sufficient accuracy is not ensured for the above character-string recognition processing.

According to the above mode, also when it is determined that some of components to be inspected are not correct components due to erroneous recognition of a character string though correct components are mounted, it is possible to conclude that the components to be inspected are correct components from a determination result on other component. It is possible to set the above "predetermined number" so as to be a constant ratio for the total number of components corresponding to the component identifying information.

Then, a substrate inspecting apparatus of the present invention has a function of inspecting whether correct components are mounted on the above substrate by receiving a component mounting substrate prepared by a component mounting machine. First, a substrate inspecting apparatus for executing the above first method comprises an entering part for entering a character string to be printed on each component, an information obtaining part for obtaining component identifying information for identifying a component replaced or replenished in the component mounting machine and substrate identifying information for identifying a specific substrate on which the replaced or replenished component is mounted, a specifying part for specifying a substrate corresponding to the substrate identifying information among supplied substrates and specifying a component to be inspected in accordance with the component identifying information, a determining part for executing processing of obtaining the image of the component to be inspected from the specified substrate and extracting a character string from the image and processing of comparing the extracted character string with a character string entered by the entering part and determining whether correct components are mounted on the substrate in accordance with the comparison result, and an outputting part for outputting inspection result information including the determination result by the determining part.

Moreover, a substrate inspecting apparatus for executing the above second method comprises an entering part for entering a character string to be printed on each component on a substrate to be inspected, an information obtaining part for receiving component identifying information for identifying a replaced or replenished component transmitted from the component mounting machine, a specifying part for specifying a component to be inspected in accordance with the component identifying information, a determining part for executing processing of obtaining the image of the component to be inspected on each of a predetermined number of substrates supplied after receiving the component identifying information and extracting a character string from the image and processing of comparing the extracted character string with a character string entered by the entering part and determining whether correct components are mounted on the substrate, and an outputting part for outputting inspection result information including the determination result by the determining part.

In the case of the apparatuses having the above configurations, it is possible to constitute each part by a computer in which a program for executing the processing of the part is built in. Moreover, it is possible to include an interface circuit for receiving each piece of identifying information from a mounter in the information obtaining part. Furthermore, it is possible to include an interface circuit for outputting inspection result information to an external device in the outputting part.

However, it is possible to include a device for reading each piece of identifying information from a predetermined storing medium in the information obtaining part of the first apparatus instead of an interface circuit. Moreover, in the case of any one of the first and second apparatuses, it is possible to include a device for storing inspection result information in a predetermined storing medium in the outputting part instead of the interface circuit. Furthermore, in the case of the first apparatus, when using a device for processing the information in a storing medium for both the information obtaining part and outputting part, it is possible to use a device common to these parts.

Moreover, it is preferable to set an imaging part for generating images of a substrate and component and a memory for entering a character string by the entering part to a substrate inspecting apparatus of the present invention. Furthermore, it is possible to store the above substrate design data and substrate inspection data in the memory. Furthermore, it is possible to enter the information for character images corresponding to a plurality of types of fonts so as to be able to correspond to various types of fonts in the processing of recognizing a character string.

When receiving a substrate corresponding to the substrate identifying information set by a component mounting machine, the first substrate inspecting apparatus executes processings of successively imaging components to be inspected specified in accordance with component identifying information, extracting a character string from the image of each component, and comparing the extracted character string with an entered character string. In the case of this apparatus, it is preferable to able to correspond to erroneous determination due to erroneous setting of substrate identifying information or erroneous recognition of a character string at a mounter so that the same inspection can be executed for a predetermined number of substrates supplied after a substrate specified in accordance with substrate identifying information.

The second substrate inspecting apparatus specifies components to be inspected, successively images the specified components to be inspected for a predetermined number of substrates to be subsequently supplied, and executes inspection according to character string recognition same as the case of the first substrate inspecting apparatus. It is possible to set the number of substrates to be inspected in accordance with the number of substrates which can be set between the apparatus and a mounter as described above. Moreover, it is preferable to set a part for inputting the number of substrates to the inspecting apparatus so that the number of the substrates to be inspected can be optionally set or changed.

In the case of the first and second apparatuses, it is possible to use the mounting position of a component, type of the component, and identifying information on a feeder to which components are supplied as component identifying information and it is possible to specify a component to be inspected by using a method corresponding to the type of the information.

In the case of preferable modes of the first and second substrate inspecting apparatuses, the entering part enters component inspection data including a character string to be printed on each component on a substrate to be inspected. However, without being restricted to the above mentioned, it is also allowed to enter, for example, data obtained by collecting only character strings of various components and link the data to substrate inspection data through type-of-component data or data conforming to the type-of-component data.

Moreover, in the case of another preferable mode, when a comparison result is obtained that the extracted character string coincides with the character string information corresponding to the components to be inspected for a predetermined number of components or more among a plurality of components specified as the above components to be inspected, it is determined that a correct component is mounted on a substrate to be inspected. Thus, even if erroneous recognition of a character string occurs in some of components to be inspected, it is possible to derive a correct conclusion in accordance with recognition results of remaining components.

It is possible to automatically set the number of components necessary for the determination that a correct component is mounted so as to be a constant ratio to the total number of components specified as components to be inspected. Without being restricted to the above mentioned, it is allowed to receive and set an input of a user.

Each of the substrate inspecting apparatuses respectively having the above-described configuration can not only execute mounting error inspection for a substrate prepared when a component is replaced or replenished but also execute inspections on various items such as the mounting position, mounting direction, electrode, and soldered state of each component for every supplied substrate. It is preferable that the above outputting part is constituted to as to determine the quality of a substrate by integrating inspection results including mounting-error inspection results and output the determination result. To output the result, it is also possible to not only transmit the result to an external device but also display the result or store the result in a storing medium.

DESCRIPTION OF THE PREFERRED EMBODIMENTS

Figure 1:
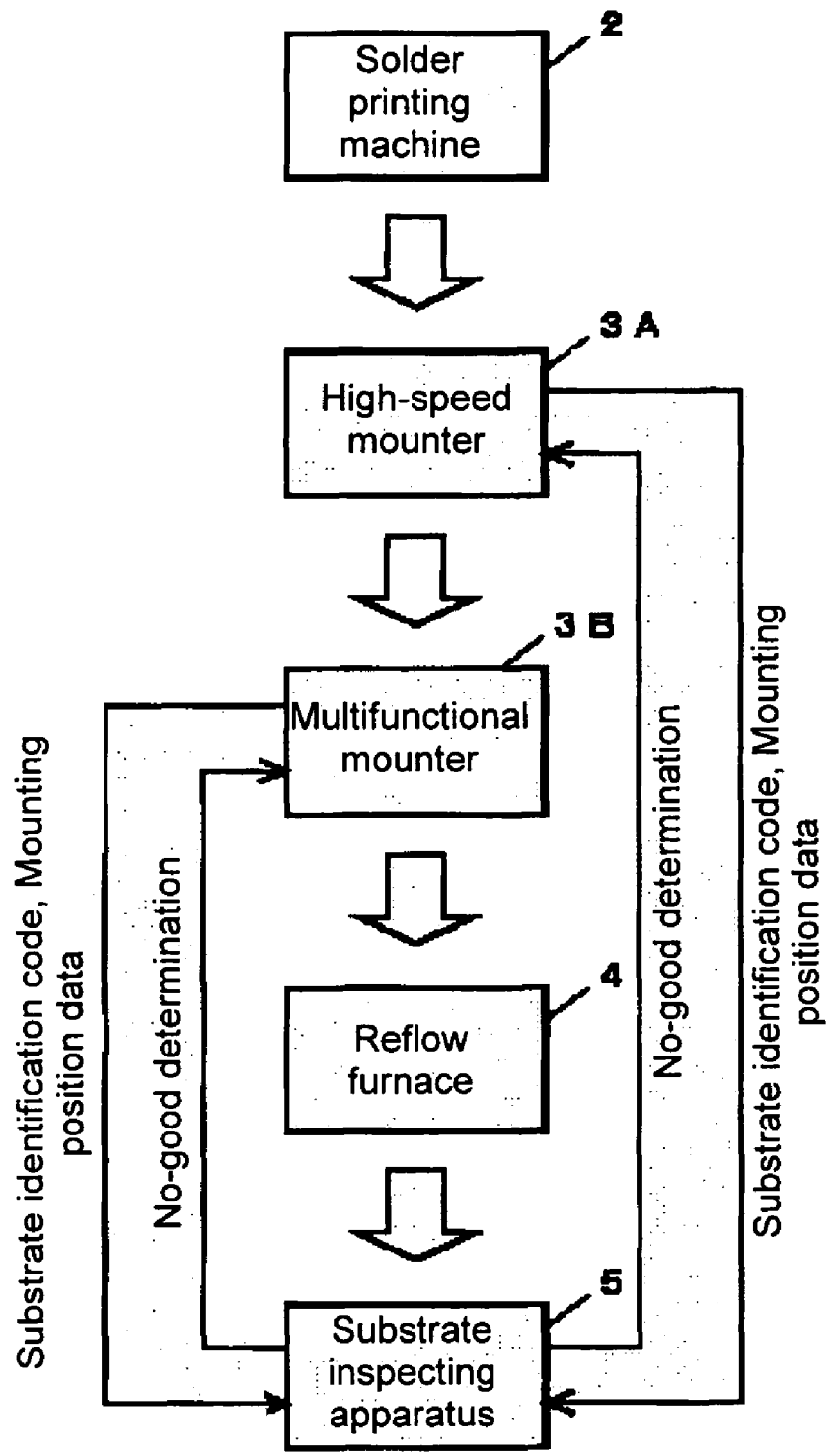
FIG. 1 shows a substrate fabricating line of the present invention together with flows of a component and information between devices.

FIG. 1 shows a flow (thick arrow) of a substrate and a flow (thin arrow) of information exchanged between devices for mounting error inspection on a substrate fabricating line applied with mounting error inspection of the present invention.

The illustrated substrate fabricating line includes a solder printing machine 2, high-speed mounter 3A, multifunctional mounter 3B, reflow furnace 4, and substrate inspecting apparatus 5. A substrate carrying conveyer (not illustrated) is set between the above installations and substrates are successively sent to each installation to undergo processing.

The solder printing machine 2 receives a printed circuit board and applies cream solder to the soldering position of each component. The high-speed mounter 3A is a device for mounting a chip component at a high speed and the multifunctional mounter 3B is used to mount components other than a chip component. The reflow furnace 4 heats a substrate passing through a component mounting step by these mounters to solder it. The substrate inspecting apparatus 5 receives a substrate passing through the above steps to execute various inspections including the mounting error inspection.

A bar code label showing the identification code specific to a substrate used for this embodiment is previously attached to the substrate. The identification code is hereafter referred to as "substrate identification code".

In the description below, the high-speed mounter 3A and multifunctional mounter 3B are generally referred to as "mounter 3" without distinguishing between them.

The above mounting error inspection is inspection for detecting a defective substrate due to an error when a component is replaced or replenished in any one of the mounters 3. This embodiment inspects whether a replaced or replenished component is a correct component for a predetermined number of substrates on each of which the replaced or replenished component is mounted.

Each mounter 3 transmits the identification code of a substrate on which a replace or replenished component is first mounted and information showing the mounting position of the component (hereafter referred to as "mounting position data") to the substrate inspecting apparatus 5 in order to execute the mounting error inspection. The substrate inspecting apparatus 5 specifies a substrate and component to be inspected in accordance with the transmitted information and executes mounting error inspection. As a result, when it is determined that there is a mounting error, the substrate inspecting apparatus 5 returns no-good determination to the mounter 3 receiving the information. The mounter 3 receiving the no-good determination notifies a user that an erroneous component is mounted by outputting predetermined warning information or interrupting the component mounting operation. Thereby, even if mounting an erroneous component, the user can early find and correspond to the error.

Figure 2:
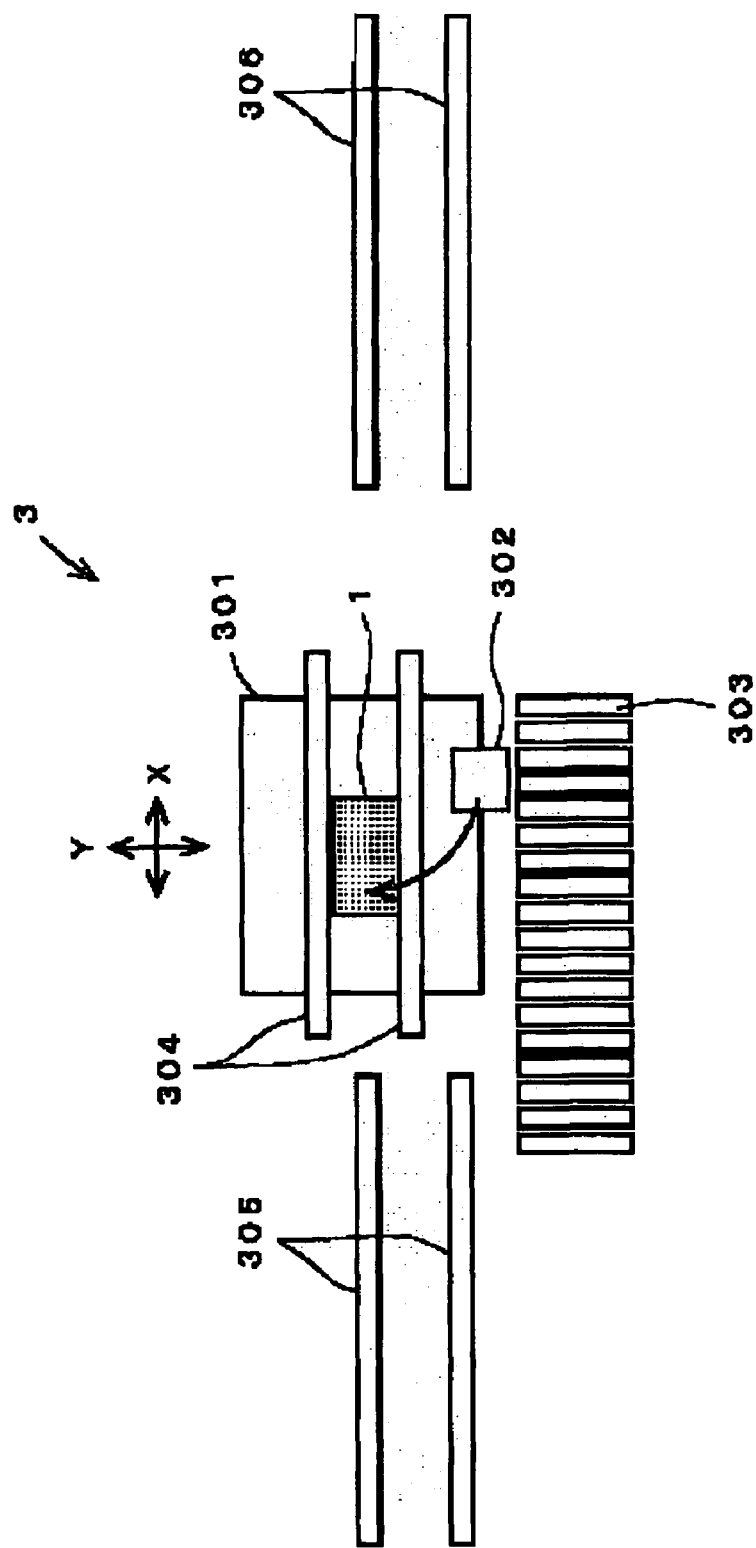
FIG. 2 shows an illustration showing a schematic configuration of a mounter.

FIG. 2 shows a schematic configuration of the mounter 3. In FIG. 2, symbol 1 denotes a substrate to be processed and 301 denotes a stage portion for supporting the substrate 1. Moreover, symbol 302 denotes a head portion for mounting a component on the substrate 1, to which an attracting nozzle (not illustrated) for attracting a component is set.

The head portion 302 is set so as to be movable in the direction along the direction for bringing in/out the substrate 1 (X-axis direction) and the stage portion 301 is set so as to be movable in the direction orthogonal to X axis (Y-axis direction). A conveyer 304 for carrying substrates is set to the stage portion 301. When bringing in/out the substrate 1, the position of the stage portion 301 is adjusted so that the conveyer 304 communicates with the upstream-side or downstream-side conveyer 305 or 306.

A plurality of tape feeders 303 is set along the bring-in/out direction of the substrate 1 nearby the head portion 302. Each tape feeder 303 has a reel on which a tape for holding a component is wound and a driving mechanism (not illustrated) for delivering a tape from the reel at a constant pitch.

Figure 3:
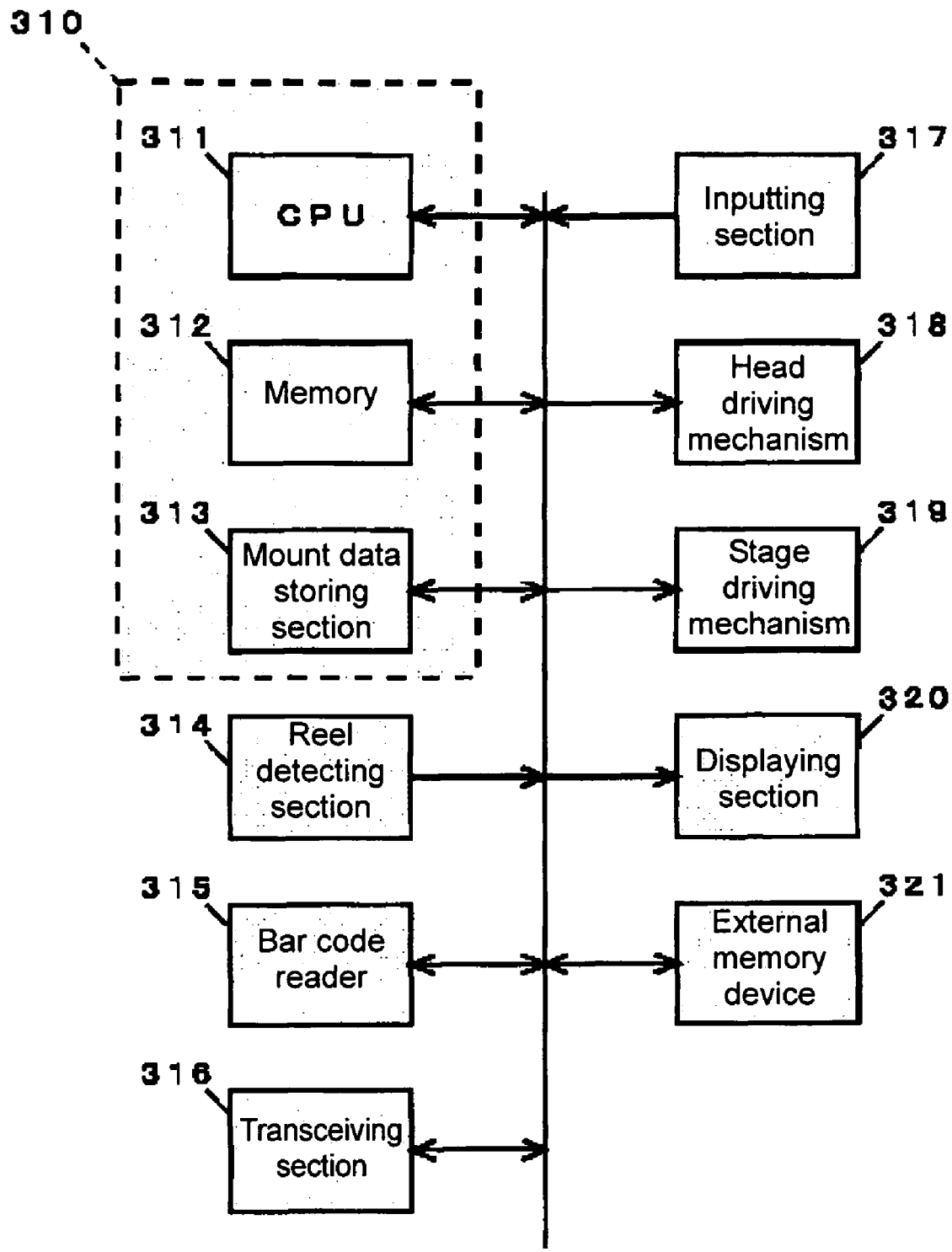
FIG. 3 shows a block diagram showing an electrical configuration of a mounter.

FIG. 3 shows an electrical configuration of the mounter 3. The controlling section 310 of the mounter 3 has not only a CPU 311, a memory 312 storing a program and the like but also a mount data storing section 313. Moreover, the mounter 3 is provided with a reel detecting section 314, bar code reader 315, transceiving section 316, inputting section 317, head driving mechanism 318, stage driving mechanism 319, displaying section 320, and external memory device 321.

The mount data storing section 313 is a memory for storing the mount data for various types of substrates. The mount data for each substrate is generated in accordance with substrate design data set by a substrate designing CAD system, in which data values such as type of component, mounting position data (generally shown by coordinates of center of gravity of component body), height of component, feeder number showing a component supply source, location name (name set at position where component is mounted) are set. It is possible to capture the mount data by a storing medium set to the external memory device 321 or communication by the transceiving section 316. Moreover, it is not always necessary to make the mount data storing section 313 independent from the memory 312 but it is allowed to physically set the section 313 in a memory device same as the memory 312.

The head driving mechanism 318 is used to move the head portion 302 along X-axis direction and the stage driving mechanism 319 is used to move the stage portion 301 along Y-axis direction. The inputting section 317 is used to input various set data values or perform the operation for staring component mounting. The displaying section 320 is used to communicate predetermined information, for example, to communicate a mounting error in accordance with no-good determination from the substrate inspecting apparatus 5.

The reel detecting section 314 is connected to a reel detecting sensor (not illustrated) set to each tape feeder 303, which is constituted so as to output a detection signal showing the state in which a reel is removed or reset in a predetermined tape feeder 303 to the CPU 311. The reel detecting sensor is constituted so as to output a signal to be turned on when a reel at whose both sides light-emitting and light-receiving sections of a photoelectric switch are set is removed. Moreover, the feeder number of each tape feeder 303 is set to the reel detecting section 314 so as to output a digital signal for relating presence or absence of a reel with the feeder number corresponding to the reel as the detection signal.

The bar code reader 315 is used to read substrate identifying data shown on the bar code label of the substrate, which is set so as to correspond to the bar code label when the stage portion 301 is present at the reference position.

The transceiving section 316 is used for communication with an external device such as the substrate inspecting apparatus 5. The external memory device 321 is used to capture set data such as the above mount data, which is constituted by a reader-writer corresponding to a predetermined storing medium such as a flexible disk or CD-R.

In the above configuration, when a component mounting step is started, mount data for the substrate 1 to be processed is read out from the mount data storing section 313 and set to the memory 312. The CPU 311 moves the head portion 302 up to a predetermined tape feeder 303 in accordance with the mount data to make an attracting nozzle attract the component. Moreover, the CPU 311 controls positions of the head portion 302 and stage portion 301 to move the component up to a position for mounting the component and then cancels attraction of the attracting nozzle to set the component on the substrate 1.

Furthermore, the CPU 311 detects removing or setting of a reel in each tape feeder 303 by using a detection signal output from the reel detecting section 314. In this case, when detecting that the reel is removed from the predetermined tape feeder 303, the CPU 311 reads out corresponding mounting-position data from the mount data in accordance with the feeder number of the tape feeder 303. Furthermore, when a reel is set to the tape feeder 303 again, the CPU 311 drives the bar code reader 315 to read a substrate identification code from a substrate to be first processed and outputs the code to the substrate inspecting apparatus 5 together with the mounting position data.

When a substrate to be fabricated is changed, new mount data is read out and set to the memory 312 and reels are replaced in many tape feeders 303. In this case, the CPU 311 refers to the newly set mount data in accordance with the feeder number of each tape feeder 303 in which reels are replaced to successively read out mounting position data values for all replaced components.

Then, a configuration of the substrate inspecting apparatus 5 and processings in this apparatus are described below in details.

Figure 4:
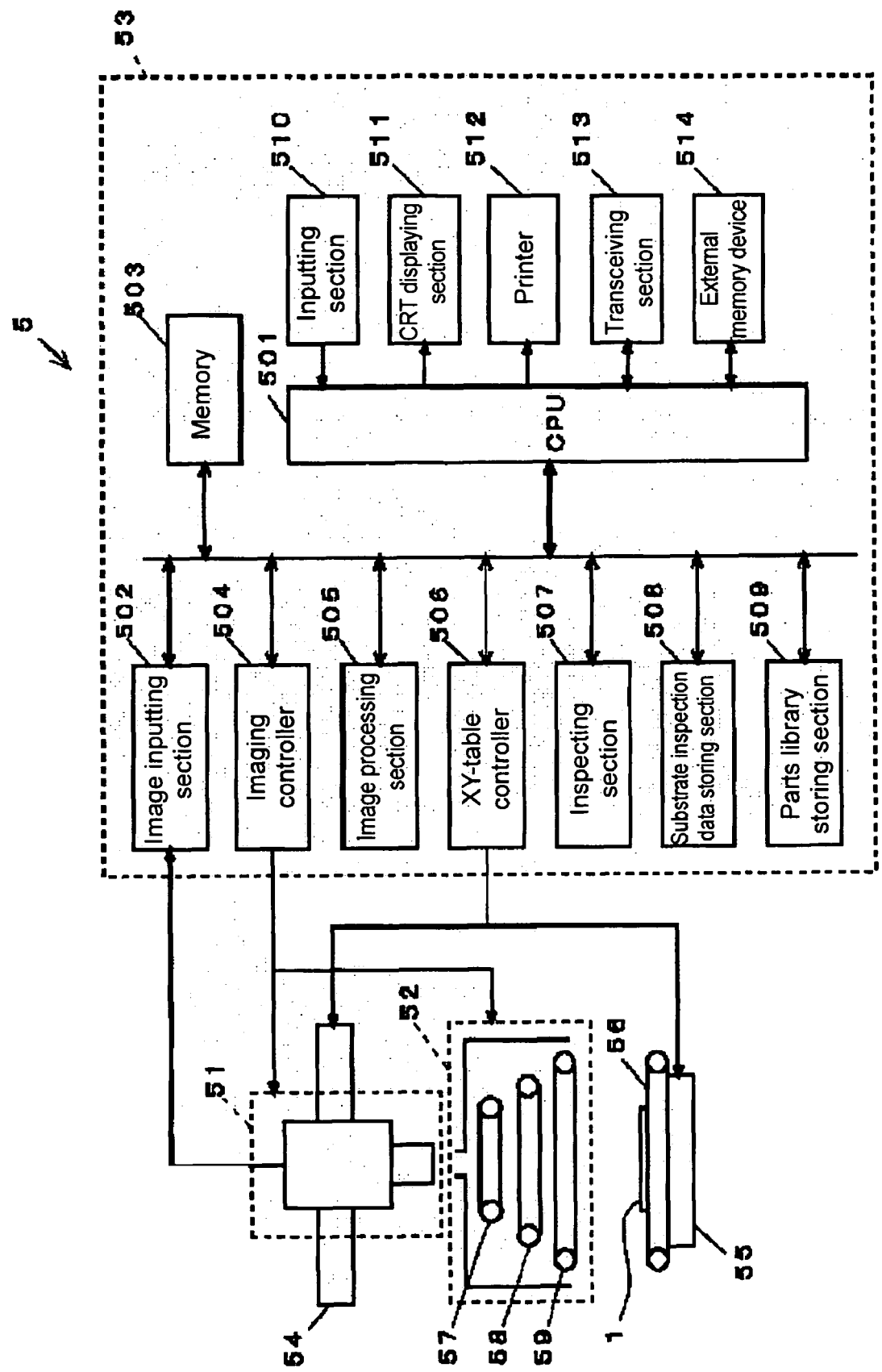
FIG. 4 shows a block diagram showing an electrical configuration of a substrate inspecting apparatus.

FIG. 4 shows a configuration of the substrate inspecting apparatus 5. The substrate inspecting apparatus 5 executes inspection by using an image obtained by imaging a substrate to be inspected, which is constituted by an imaging section 51, light projecting section 52, controlling section 53, X-axis table section 54, and Y-axis table section 55.

The Y-axis table section 555 has a conveyer 56 for supporting the substrate 1 and moves the conveyer 56 by a not-illustrated motor to move the substrate 1 in Y-axis direction (direction orthogonal to paper surface in FIG. 1). The X-axis table section 54 moves the imaging section 51 and light projecting section 52 in X-axis direction (horizontal direction in FIG. 1) while supporting the sections 51 and 52 above Y-axis table section 55.

The light projecting section 52 is constituted by three annular light sources 57, 58, and 59. These light sources 57, 58, and 59 emit color lights of red, green, and blue respectively, which are set so as to be located in directions corresponding to different elevation angles viewed from the support face of the substrate 1 by adjusting the center to the position immediately above an observing position.

The imaging section 51 is a CCD camera for generating a color image, whose optical axis corresponds to the center of the light sources 57, 58, and 59 and which is positioned in the vertical direction. Thereby, the light reflected from the substrate 1 to be observed enters the imaging section 51 and is converted into color image signals of three primary colors of R, G, and B and input to the controlling section 53.

The controlling section 53 is a computer using a CPU 501 as a control main body, which is constituted by an image inputting section 502, memory 503, imaging controller 504, image processing section 505, XY-table controller 506, inspecting section 507, substrate inspection data storing section 508, parts library storing section 509, inputting section 510, CRT displaying section 511, printer 512, transceiving section 513, and external memory device 514.

The image inputting section 502 has an amplifier for amplifying image signals of R, G, and B output from the imaging section 51 and an A/D converting circuit for converting these image signals into digital signals. The memory 503 stores digital-value shading image data every R, G, and B and a binary images obtained by digitizing these shading images, which is used to temporarily store transmission information supplied from the mounter 3 and an intermediate result of inspection or enter various fonts used for mounting-error inspection.

The imaging controller 504 has an interface for connecting the imaging section 51 and light projecting section 52 to the CPU 501 to perform controls of adjusting the luminous energy of each light source of the light projecting section 52 in accordance with an instruction output from the CPU 501 and keeping the mutual balance between color light outputs of the imaging section 51.

The XY-table controller 506 includes an interface for connecting the X-axis table section 54 and Y-axis table section 55 to the CPU 501 to control movements of the X-axis table section 54 and Y-axis table section 55 in accordance with an instruction output from the CPU 501.

The substrate inspection data storing section 508 is a memory for entering the substrate inspection data set for each type of substrate. The substrate inspection data every substrate is constituted by storing component inspection data for each component to be mounted on a corresponding substrate in a data file provided with a predetermined file name (hereafter referred to as "inspection data file").

The parts library storing section 509 is a memory for hierarchizing preset standard component inspection data (hereafter referred to as "reference component inspection data") and entering the data. Specifically, various types of components are segmentalized into a plurality of variations related to types of components respectively and various inspection data values are related and entered.

In the case of this embodiment, to generate the above substrate inspection data, corresponding reference component inspection data is read out from the parts library storing section 509 for each component on a substrate and related to the mounting position of the component. However, the inspection data for the above erroneous component inspection is set in accordance with the data which a user inputs while referring to the image of an actual component.

The image processing section 505 extracts gradations of R, G, and B and the lightness shown by the total sum of these gradations from image data values of R, G, and B stored in the memory 503 every pixel. Moreover, the section 505 executes processing of setting an inspecting window in accordance with the component inspection data for each component and extracting color patterns of R, G, and B in the window and processing of calculating characteristic of the extracted color patterns.

The inspecting section 507 performs quality determination by comparing a characteristic value extracted in the inspecting window with a reference value and outputs the determination result to the CPU 501. The CPU 501 determines the quality of each component by integrating determination results in inspecting windows and moreover finally determines whether the substrate 1 is a good or bad product in accordance with these determination results. The final determination result is output to the CRT displaying section 511, the printer 512, or transceiving section 513.

The inputting section 510 is used to input various conditions for inspections and inspection information and constituted by a keyboard and mouse. The CRT displaying section 511 (hereafter merely referred to as "displaying section 511") receives image data and inspection results from the CPU 501 and data from the inputting section 510 and displays these data values on a display screen. Moreover, the printer 512 receives inspection results from the CPU 501 and prints out the results in accordance with a predetermined format.

The transceiving section 513 is used to transfer data to and from an external device such as the mounter 3. The external memory device 514 is a reader-writer for a predetermined storing medium such as a flexible disk, CD-R, or magneto-optical disk, which is used to store the inspection results or capture programs necessary for inspections and set data from external devices.

In the above configuration, the image processing section 505 and inspecting section 507 are respectively constituted by a dedicated processor in which programs for executing the above processings are built. However, it is not always necessary to use the dedicated processor. It is allowed to add functions of the image processing section 505 and inspecting section 507 to the CPU 501. Moreover, it is not necessary to physically individually set the memory 503, substrate inspection data storing section 508, or parts library storing section 509 but it is possible to set them in the same memory device (such as hard disk drive).

In the above substrate inspecting apparatus 5, the component inspection data for each component includes the mounting direction (shown by tilt of component from predetermined reference direction) and coordinates of a corresponding component, inspecting-window setting data, parameters used for inspections (such as binary threshold values necessary to extract color patterns of R, G, and B and program used to extract characteristics of color patterns; the parameters are hereafter referred to as "inspection parameters"), a criterion for determining qualities of color patterns extracted in accordance with the inspection parameters, and a variation name showing the position of the data read out from the parts library strong section 509 to se the component inspection data. Moreover, a character string printed on a component body and the type of the font of the character string are set to the component inspection data for this embodiment for the above mounting error inspection.

Figure 5:
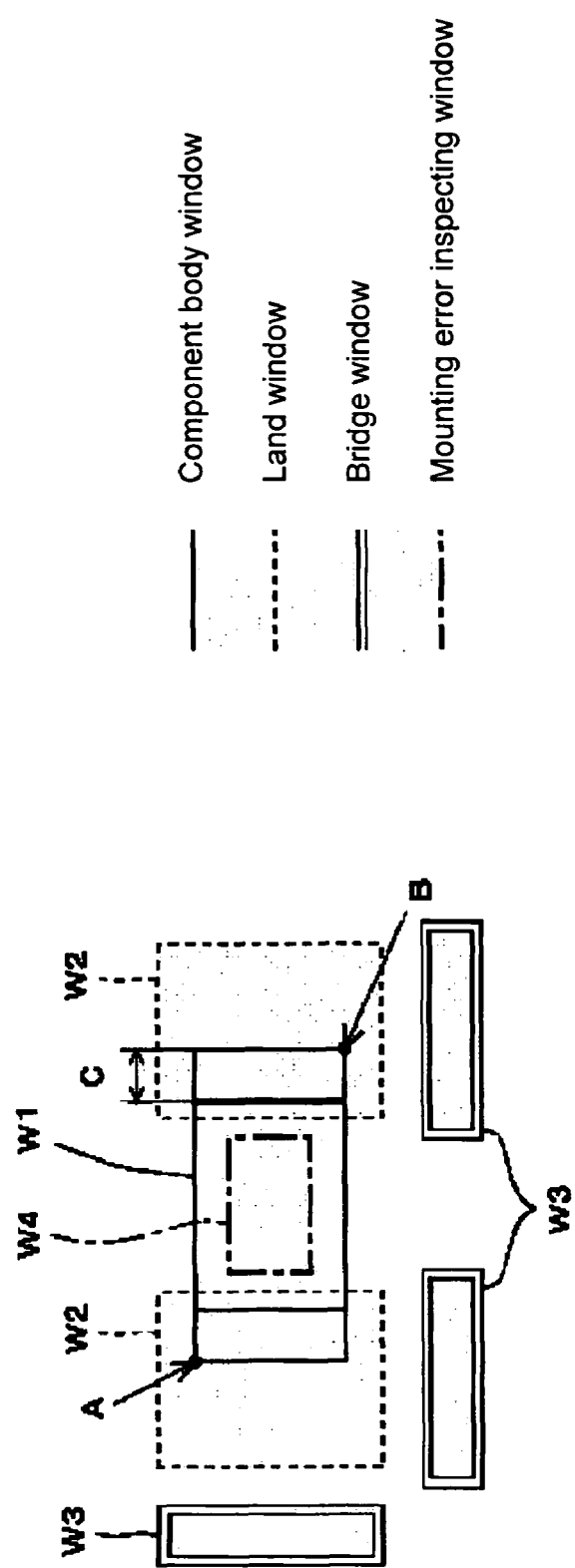
FIG. 5 shows an illustration showing set examples of inspecting windows.

FIG. 5 shows set examples of inspecting windows of a chip component. In FIG. 5, a window W1 shown by a continuous line is a component body window which is used to inspect presence or absence of a component body, advisability of mounting direction of the body, and displacement of the body from an electrode. The data for setting the window W1 denotes coordinates having vertexes A and B which are opposite angles to each other. Because it is necessary to extract the relation between the electrode and component body, the width C of the electrode portion is also entered as set data.

A window W2 shown by a dotted line is a window for determining a soldered state, a window W3 shown by a double line is a window for detecting a solder bridge for a peripheral component. These windows W2 and W3 also use coordinates of vertexes which are opposite angles to each other as set data the same as the case of the component body widow W1.

A window W4 shown by an alternate long and short dash line is a window for mounting error inspection. The window W4 (hereafter referred to as "mounting-error inspecting window") is set by being related to the printing position of a character string on a component body.

In the case of this embodiment, the set data for windows W1, W2, and W3 among the above inspecting windows, inspection parameters to be applied to these inspecting windows, and criteria are standard-set as the reference component inspection data for the parts library and only the inspection data for mounting error inspection is set in accordance with operations by an operator. However, without being restricted to the above mentioned, it is possible to include the set data for the mounting-error inspecting window W4 and the data for the character strings and types of fonts in the reference component inspection data.

Because a mounting position shown by the mounting position data transmitted from the mounter 3 corresponds to the position of the center of gravity of a component body, the mounting position is included in the component body window W1. According to the principle, in the case of the mounting error inspection in this embodiment, component inspection data set so that the component body window W1 includes the mounting position data is extracted so as to specify a component corresponding to the component inspection data as an object for mounting error inspection. Mounting error inspection for each component is executed by a method for determining the advisability of a character string printed on the component as ever.

Figure 6:
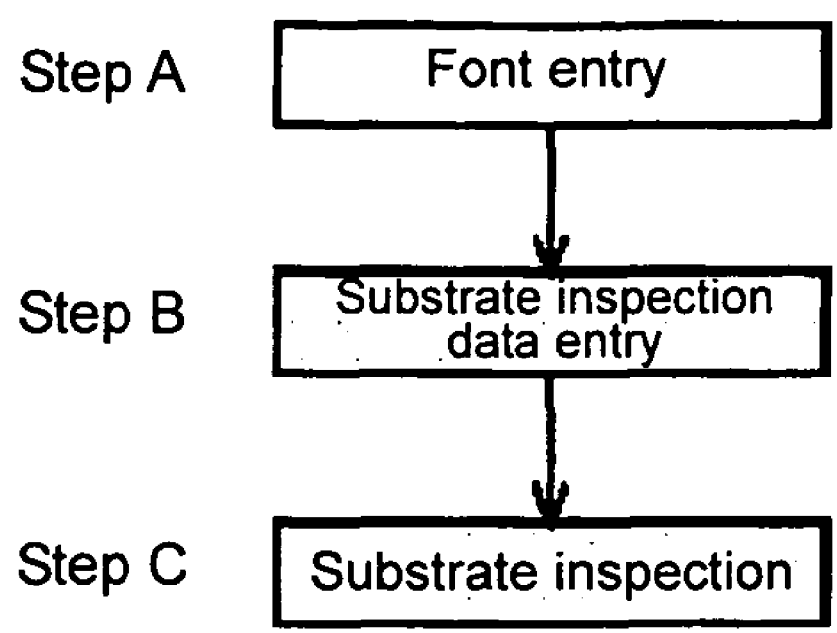
FIG. 6 shows illustrations showing a flow of a large processing in a substrate inspecting apparatus.

FIG. 6 shows a series of processing procedures from an initial state up to a state ready for inspection in the substrate inspecting apparatus 5. In FIG. 6, in the first step A, font entry processing for mounting error inspection is executed. In the step A, processing is executed in which an actual component is imaged and displayed on the displaying section 511 and characters in the image are cut out one character by one character and entered in accordance with operations by an operator. For example, it is possible to enter a font for each component maker. It is also allowed to previously prepare the font by an apparatus separate from the substrate inspecting apparatus 5, capture the font through communication or from the above storing medium and enter it.

In the next step B, substrate inspection data is generated for a substrate to be inspected and entered in the substrate inspection data storing section 508. Then, in the step C, substrate inspection is executed by using the substrate inspection data and the font entered in the step A. The steps B and C will be described later in detail.

Figure 7:
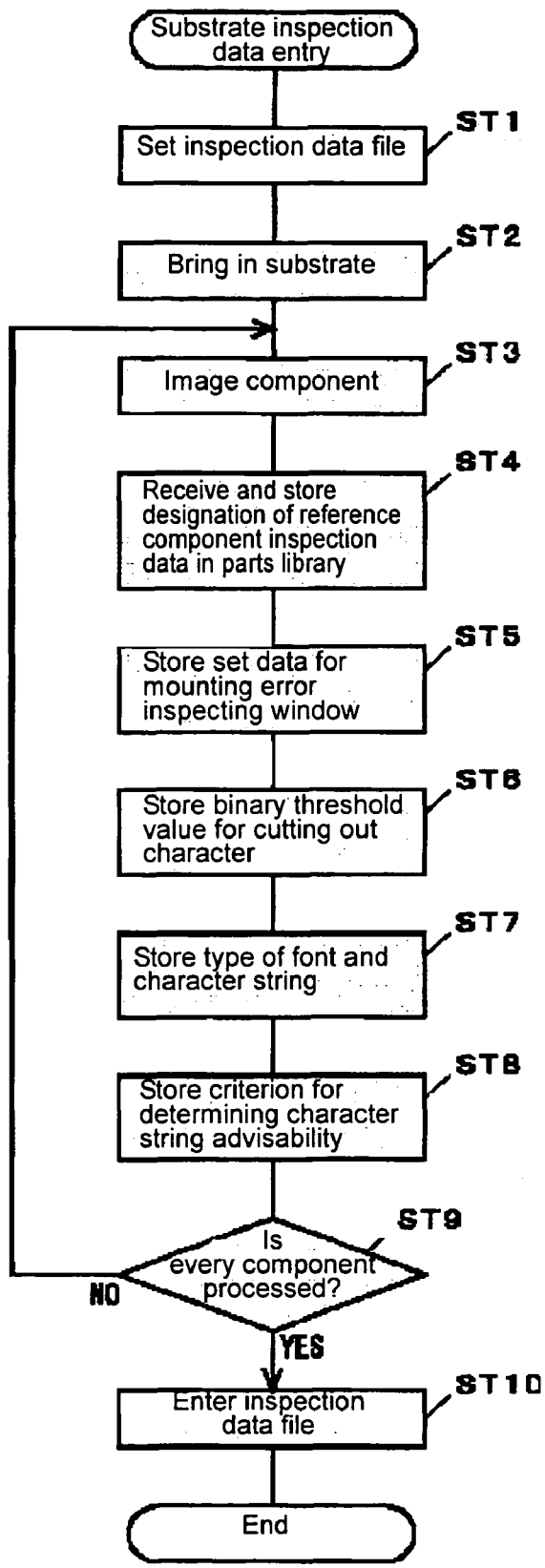
FIG. 7 shows a flowchart showing a procedure for entry of substrate inspection data.

FIG. 7 shows a detailed procedure for the entry processing of the substrate inspection data in the step B. In FIG. 7, steps are shown as ST1 to ST10. Moreover, because the procedure corresponds to one type of substrate, it is necessary to execute the procedure every substrate in order to enter the substrate inspection data for a plurality of substrates.

The substrate inspection data for this embodiment is generated by using a substrate (this substrate is hereafter referred to as "reference substrate") of a model on which correct components are mounted and in which the mounted state of each component is preferable. The procedure in FIG. 7 is started in accordance with an operation for an operator to input a predetermined file name, in which a vacant inspection data file provided with an input file name is set to the memory 503 in ST1. Then, when the operator sets the reference substrate to a predetermined position and perform the starting operation, the reference substrate is brought onto the Y-axis table 55 in ST2. Thereafter, steps ST3 to ST8 are successively executed for components on the reference substrate.

First, the operator positions the imaging section 51 and light protecting section 52 to the components to be processed to execute the setting start operation. According to the operation, ST3 is started to store a color shading image received from the imaging section 51 in the memory 503 by digital-converting the image and display the digital-converted image on the image to be stored on the displaying section 511.

In this case, the operator designates corresponding reference component inspection data in the parts library 509. In ST4, the designated reference component inspection data is read out and stored in the inspection data file as the inspection data for the above components. The data values set in the inspecting windows W1 to W3 in the inspection data are set as relative coordinates corresponding to a predetermined reference point. However, when the set data is stored as actual inspection data, coordinate data is rewritten in accordance with mounting positions of the components.

Then, the operator designates a region in which character strings printed on the component bodies are included on images of the components. In ST5, the designated region is recognized as the mounting error inspecting window W4 to store the set data in the inspection data file.

In the next ST6, binary threshold values for cutting out characters in the mounting error inspecting window W4 are set to store the values in the inspection data file. In this ST6, it is possible to set binary threshold values every R, G, and B in accordance with gradations of designated pixels in accordance with the operation for designating pixels constituting character strings in the mounting error inspecting window W4. Moreover, it is possible to decide binary threshold values in accordance with the average value of gradations of pixels by designating a plurality of pixels.

In the next ST7, types of fonts corresponding to the character strings and the character strings are stored in the inspection data file. It is possible for the operator to input the information to be stored while referring to the image display. However, without being restricted to the above mentioned, it is also allowed to recognize the character strings extracted in accordance with the binary threshold values by collating them with the font entered in the step A, display the recognition results to make the operator confirm the results, and then store them.

In the next ST8, criteria for determining that character strings to be processed are correct in the above character string collation are set to store the values in the inspection data file. The above criteria can include not only a criterion (similarity) for determining that a cut-out character coincides with the character image of a predetermined font but also a criterion (e.g. the number of characters obtaining coincidence determination) for determining the final recognized character string coincides with the character string stored in the inspection data file. Though the operator can input these criteria, it is also allowed to previously set a default criterion, change the criterion in accordance with the change operation by the operator, and store the criterion in accordance with the decision operation.

Thus, processing in ST3 to ST8 are executed for each component on the reference substrate to set the inspection data for each component and store the data in the inspection data file. When processings for all components are completed, ST9 becomes "YES" and ST10 is started to enter the inspection data file in the substrate inspection data storing section 508 and complete the processing.

Figure 8:
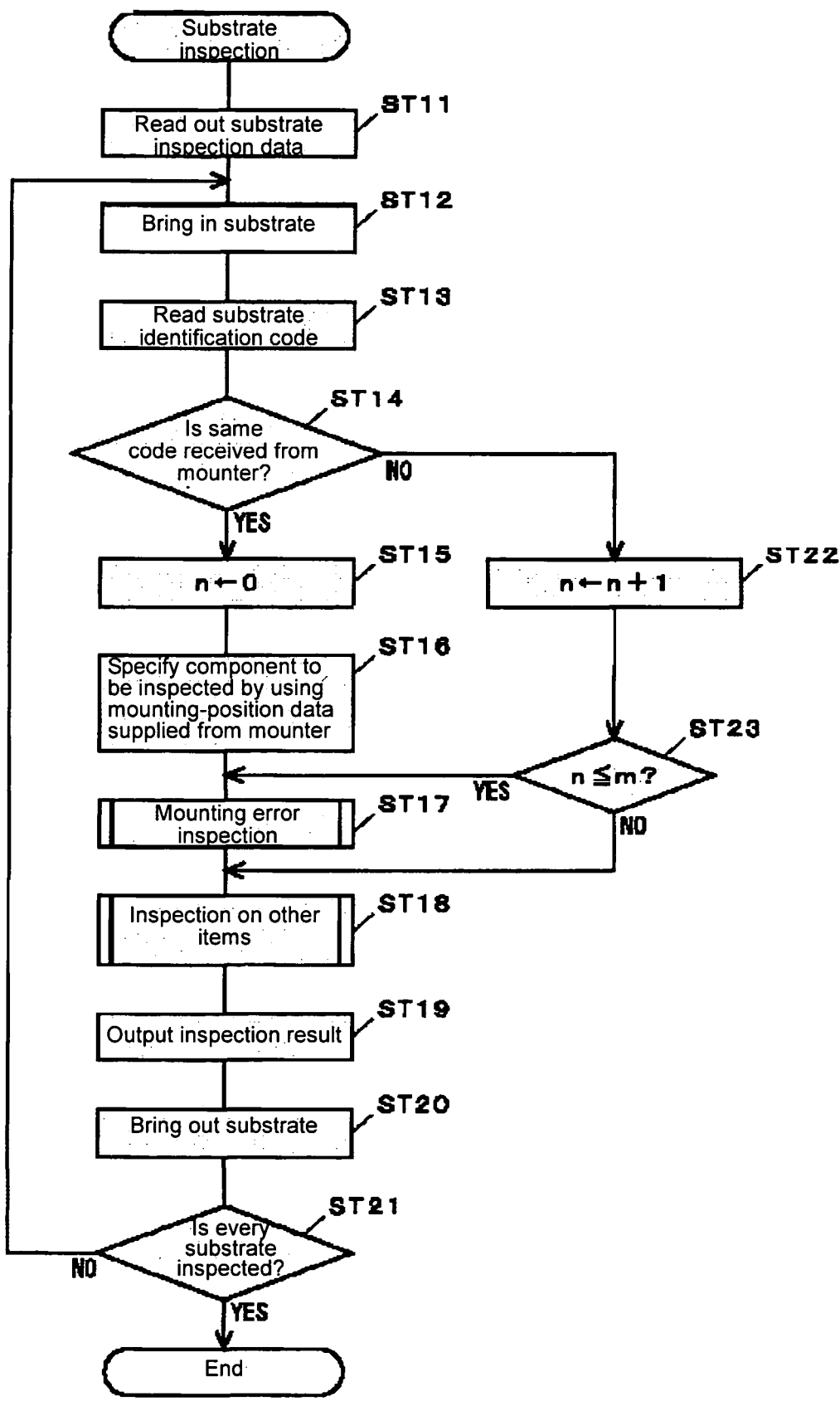
FIG. 8 shows a flowchart showing a procedure for substrate inspection.

FIG. 8 shows a procedure for the substrate inspection in the step C. Though not illustrated in FIG. 8, the substrate inspecting apparatus 5 of this embodiment can receive substrate identification codes and mounting position data from the mounter 3 at any timing when the apparatus 5 is in a state capable of starting an inspection procedure or while the apparatus 5 executes inspections. The information received from the mounter 3 is stored in the temporary strong area of the memory 503 and kept until processing of a substrate corresponding to the information is completed or the next information is received.

At start of the inspection, the operator designates the type of a substrate to be inspected in accordance with the substrate name or the like. The procedure in FIG. 8 is started in accordance with the designation operation. In the first ST11, the inspection data for the designated substrate is read out and set to the memory 503. When the inspection start operation is executed under the above state, actual substrates 1 are successively received to execute processings ST12 to ST20.

In ST12, the first-carried substrate 1 is brought into the Y-axis table section 55 to start imaging. In the case of this embodiment, the imaging section 51 is first positioned to the position of the bar code label of the substrate 1 to read the substrate identification code (ST13).

In this case, the first-carried substrate 1 is a substrate first processed in the component mounting step. When assuming that component replacement is performed in the mounter 3 to prepare the substrate 1, a code same as the substrate identification code read in ST13 is transmitted from the mounter 3. Thereby, ST14 becomes "YES" and a counter n is reset in ST15.

The counter n is used to count the number of substrates processed after a substrate corresponding to the substrate identification code transmitted from the mounter 3 (the number of substrates is hereafter referred to as "processed number of substrates"). The purpose for counting the processed number of substrates n will be described later.

After setting the processed number of substrates n, in ST 16, a component to be inspected is specified in accordance with the substrate identification code and the mounting position data transmitted from the mounter 3. In the case of the specification, data in which the component body window W1 is set so as to include the mounting position shown by the mounting position data is extracted from the component inspection data values in substrate inspection data.

Because a predetermined number of same components are generally mounted on a substrate, a plurality of mounting-position data values is transmitted from the mounter 3. Thereby, in ST16, a plurality of components to be inspected is specified.

When components to be inspected are specified, ST17 is started to execute mounting error inspection for these components.

Figure 9:
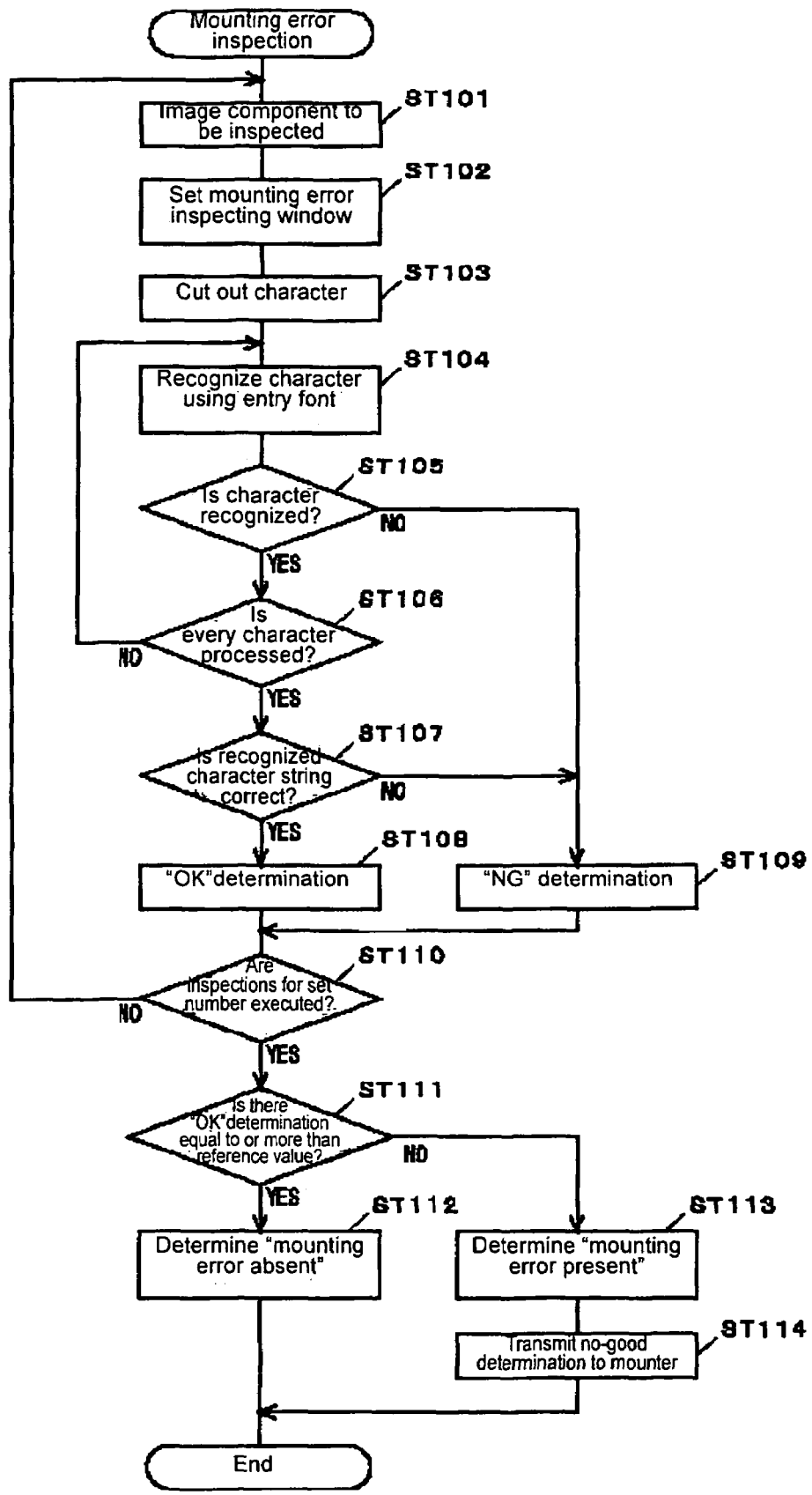
FIG. 9 shows a flowchart showing a detailed procedure for mounting error inspection.

A detailed procedure for the mounting error inspection in ST17 is described below by referring to FIG. 9. FIG. 9 shows ST17 by segmentalizing ST17 into steps ST101 to TS113.

First in ST101, the imaging section 3 is positioned to one of the components to be inspected specified in ST16 to execute imaging. In the next ST102, the mounting-error inspecting window W4 is set on images of the components. In the next ST103, images in the mounting-error inspecting window W4 are digitized to cut out characters constituting a character string by using the obtained binary images. In the case of this embodiment, color images are generated. To cut out a character, however, it is allowed to select and use a character in which most pixels corresponding to the character are extracted among binary images of R, B, and B. Moreover, to cut out a character, it is possible to apply an existing method such as a method for project a binary image in X-and Y-axis directions and recognizing an image region for one character in accordance with the peak of the projected image.

In this case, when a predetermined number of characters are cut out, the processing in ST104 is successively executed for the characters. In this ST104, collation using a plurality of character images set as entered fonts is successively executed for the image of each cut-out character to use the character shown by the character image when obtaining the similarity exceeding the above criterion as a recognition result. When a character is recognized as described above, ST105 becomes "YES" and the next character recognition is started by returning to ST104 through ST106.

When recognition of all characters is completed, ST106 becomes "YES" and a recognized character string is collated with an entered character string included in the component inspection data in ST107. In this case, when it is determined that the recognized character string coincides with the entered character string, ST107 becomes "YES" and ST108 is started to determine that components to be inspected are correct components ("OK" determination). However, when it is determined that the recognized character string is different from the entered character string, ST107 becomes "NO" and it is determined that the components are incorrect components (NG determination) in ST109.

In the process of recognizing each character, when coincidence determination is not obtained for any character image included in entered fonts on predetermined characters, ST105 becomes "NO" and ST109 is started to execute "NG" determination.

In the case of this embodiment, the above determination processing is executed for a predetermined number of components to be inspected among the above specified components to be inspected. The loop of ST101 to ST110 is repeated until inspection of the set number of components is completed and then ST111 is started to check whether "OK" determination of a predetermined criterion or more. When the above determination is "YES", ST112 is started to execute the final determination of "mounting error absent".

However, when the number of times in which "OK" determination is obtained is smaller than the above criterion, ST111 becomes "NO" and ST113 is started to execute the final determination of "mounting error present". Moreover, in this case, the above no-good determination is transmitted to the mounter 3 in the next ST114.

It is possible to previously set rates of the set number and criteria used in the above ST110 and ST111 so that the rates are always constant for all components to be inspected. However, without being restricted to the above mentioned, it is also allowed to receive an input from an operator and enter the input value by including the value in the above substrate inspection data when the data is generated.

In FIG. 8 again, when the above mounting error inspection is completed, inspection on other items (hereafter referred to as "general inspection") is executed in the next ST18. The general inspection inspects all the components on the substrate 1 and executes the inspection of successively positioning the imaging section 3 to components and thereby setting the inspecting windows W1 to W3 to images of the components, and applying a corresponding inspection parameter and criterion to each inspecting window. Because detailed procedure of the inspection is the same as the inspection executed by the conventional substrate inspecting apparatus 5, detailed illustration and description are omitted.

Thus, when inspections in ST17 and ST18 are completed, results of these inspections are integrated and the quality of the substrate 1 is determined to output the determination result in ST19. Thereafter, in ST20, the substrate 1 is brought out from the Y-axis table 7 to complete the processing for the substrate 1.

When the substrate 1 is determined to be no-good, it is preferable to output detailed information showing the no-good content in ST19.

After inspection on the first substrate 1 is completed, substrates 1 from the second substrate 1 downward are similarly brought in ST12 and imaged in ST12, and the substrate identification codes are read in ST13 to execute inspection for the substrates 1. As a result, when inspections on all substrates 1 are completed, ST21 becomes "YES" to complete processing.

For most of the substrates 1 from the second one downward, their substrate identification codes are not transmitted from the mounter 3. Therefore, ST14 becomes "NO" and ST22 is started to add 1 to the processed number of substrates n. Moreover, in ST23, the updated processed number of substrates n is compared with a predetermined number of substrates m. In this case, when n is equal to or smaller than m, ST23 becomes "YES" and ST17 is started. However, when n is larger than m, ST22 becomes "NO" and ST18 is started.

According to the above procedure, also after inspections of substrates corresponding to the substrate identification code transmitted from the mounter 3 are completed, mounting error inspection is executed for subsequent m substrates. Unless any mounting error is detected in inspections on m+1 substrates including the first substrate, it is possible to skip mounting error inspection and execute only the normal inspection for subsequent substrates.

Moreover, in the mounter 3, when predetermined components are consumed and reel replacement for replenishing components is performed, new substrate identification codes and mounting position data are transmitted from the mounter 3 in accordance with the above replacement. When a substrate corresponding to the transmission is brought into the substrate inspecting apparatus 5, ST14 becomes "YES" again and mounting error inspection is executed for replenished components. Also in this case, mounting error inspection is executed for the same components on the subsequent m substrates.

According to the above control, when reel replacement is performed at the mounter 3, mounting error inspection is executed for only components of a replaced reel on a predetermined number of substrates prepared immediately after the above replacement. Therefore, only substrates and components which must be confirmed are inspected and it is possible to improve the inspection efficiency. Moreover, because components not to be replaced or replenished are not inspected, disinformation due to the fact that these clearly correct components are erroneously recognized as incorrect components is not generated and thus, it is possible to improve the inspection accuracy.

It is possible to decide the number of substrates m to which mounting error inspection will be applied in accordance with the accuracy of character recognition. However, it is possible to set the number of substrates m to a value much smaller than the total number of substrates to be inspected. Moreover, it is preferable that a user can freely set or change the value m by using the inputting section 510.

In the case of the above embodiment, a substrate for which mounting error inspection is executed is specified by using the fact that a bar code label is attached to a fabricated substrate. However, a bar code may not be attached to a substrate depending on a substrate maker. In this case, it is possible to transmit only mounting position data from the mounter 3. Therefore, it is necessary to change inspection procedures correspondingly to the above mentioned as shown in FIG. 10.

Figure 10:
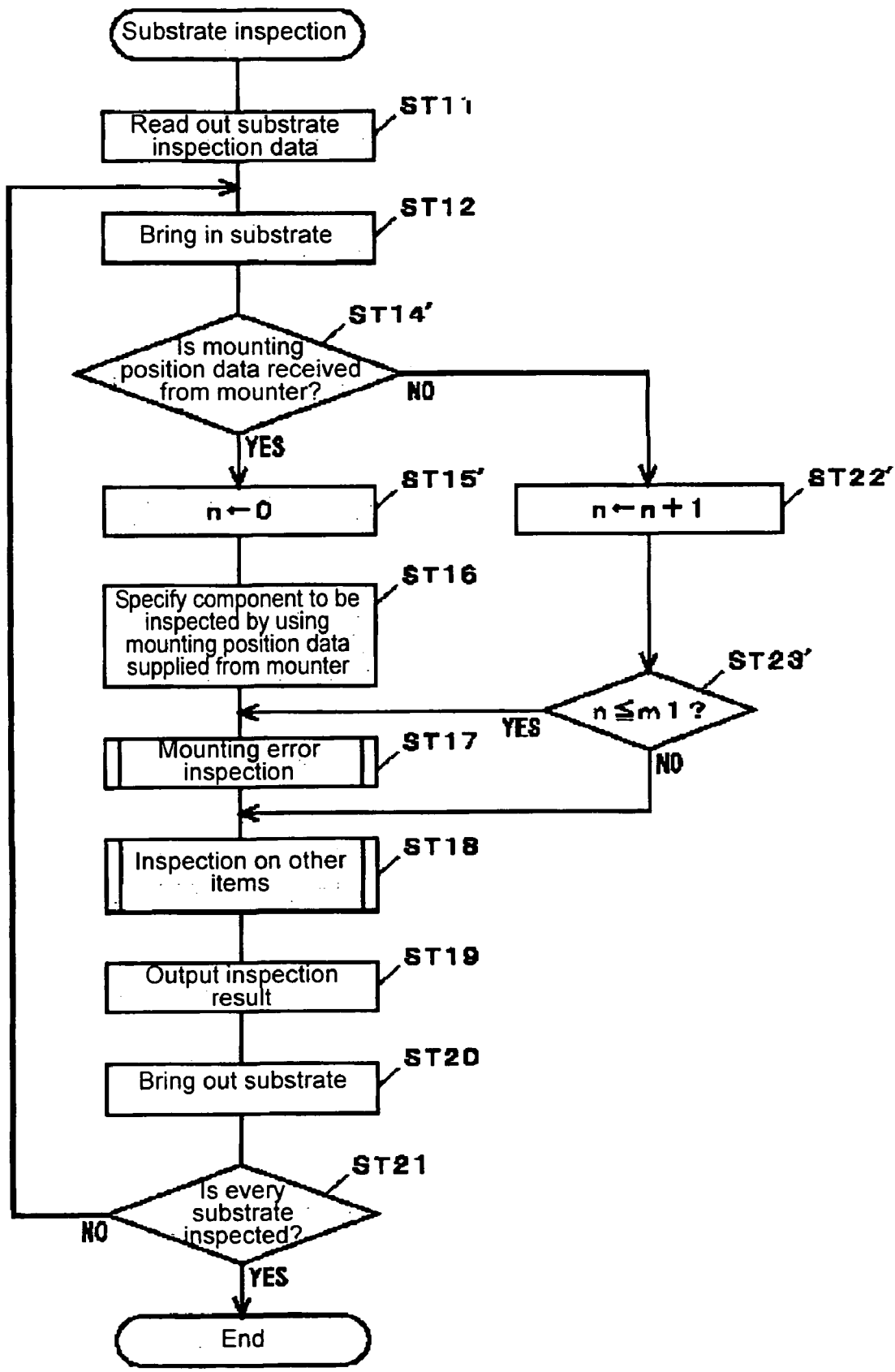
FIG. 10 shows a flowchart showing another procedure for substrate inspection.

FIG. 10 does not include a step corresponding to ST13 in FIG. 8. Moreover, a step changed from the procedure in FIG. 8 is provided with symbol ('). Other steps not changed are provided with symbols same as those in FIG. 8 and their descriptions are omitted.

In this procedure, it is checked whether mounting position data is transmitted from the mounter 3 whenever a substrate is brought in. In this case, when confirming transmission of mounting position data, ST14' becomes "YES" and the processed number of substrates n is reset in T15' and T16 is started.

When mounting position data is not received, ST14' becomes "NO" and T22' is started to update the processed number of substrates n to a value obtained by adding 1 to n. Moreover, the updated n is compared with a predetermined value m1 in ST23'. When n is equal to or smaller than m1, ST17 is started to execute mounting error inspection. However, when n is larger than m1, ST18 is started to skip mounting error inspection and execute only general inspection.

It is preferable to set m1 to the maximum number of substrates which can be located on the route between the mounter 3 serving as the transmission source of the mounting position data and the substrate inspecting apparatus 5 or a value obtained by adding a predetermined number of substrates to the maximum number of substrates. The maximum number of substrates strictly depends on whether the transmission source of information is the high-speed mounter 3A or the multifunctional mounter 3B. Therefore, it is preferable to change the value of m1 in accordance with the type of the mounter 3. Moreover, it is preferable that a user can freely set or change the value of m1 by using the inputting section 510 the same as the value of m used for FIG. 8.

According to the above procedure, it is possible to continue mounting error inspection from the time when the mounting error inspection is started with the substrate 1 to be processed immediately after receiving mounting position data until the time when the substrate 1 on which a replaced or replenished component is mounted securely arrives. Therefore, it is possible to execute efficient and accurate mounting error inspection for a substrate with no bar code label attached.

Moreover, for mounting error inspection, it is possible to perform the following design change.

First, because mounting position data is also included in substrate design data, it is also allowed to previously enter the substrate design data for a substrate to be inspected in the memory 503 and specify a component to be inspected by referring to the substrate design data in accordance with the mounting position data transmitted from the mounter 3.

Moreover, it is possible to use a type of component instead of the mounting position data transmitted from the mounter 3 as the data for specifying a component to be inspected. In this case, the substrate inspecting apparatus 5 can specify a component to be inspected by using substrate design data and thereby extracting the mounting position data corresponding to the transmitted type of component.

Furthermore, by entering mount data in the substrate inspecting apparatus 5, it is also possible to transmit the feeder number for the tape feeder 503 in which reel replacement is performed from the mounter 3. In this case, the substrate inspecting apparatus 5 can specify a component to be inspected by extracting the mounting position data corresponding to the feeder number from the mount data.

According to a type of component or feeder number, it is possible to express the information for specifying a plurality of same-type components to be inspected as one piece of information. Therefore, it is possible to improve the efficiency for referring to mount data in the mounter 3 or transmitting data. Moreover, reception processing in the substrate inspecting apparatus 5 is executed in a short time.

As described above, after specifying a component to be inspected by using substrate design data or mount data, it is necessary to refer to substrate inspection data by using the mounting position data for the specified component and execute mounting error inspection after reading inspection data necessary for the inspection.

Then, in the case of this type of the substrate fabricating line, a plurality of components having the same function may be selected and used without restricting the number of components used for each mounting position to one. In this case, a character string and font are different for each component used. Therefore, it is necessary to set inspection data to component inspection data for each component. Moreover, at the time of inspection, it is recommended to recognize and collate character strings by successively applying these inspection data values and determine "mounting error absent" when it is determined that a recognized character string coincides with the entered character string of any component.

Moreover, in the case of the above embodiment, mounting error inspection is executed after soldering. However, without being restricted to the above mentioned, it is also allowed to execute mounting error inspection for a substrate passing through a component mounting step but before entering a soldering step. In this case, when a mounting error is detected, it is possible to quickly correspond to the error. Furthermore, because soldering is not performed yet, it is possible to easily correct a defective component.

According to the present invention, when a predetermined component is replaced or replenished in a component mounting step, inspection is executed only for the component mounted on a substrate after the component is replaced or replenished, it is possible to greatly improve the accuracy and efficiency of mounting error inspection.

What is claimed is:

1. A mounting-error inspecting method for inspecting whether a correct component is mounted on a component mounting substrate passing through a component mounting step, comprising:

setting component identifying information for identifying a component and information for identifying a specific substrate on which the component is mounted when processing of replacing or replenishing the component is executed in the component mounting step;

obtaining the component identifying information and substrate identifying information set in the component mounting step in an inspecting step on whether the correct component is mounted on the substrate, wherein a substrate corresponding to the substrate identifying information is specified among supplied substrates;

executing the inspection step for the substrate;

specifying a component to be inspected in accordance with the component identifying information;

obtaining the image of the component to be inspected;

extracting a character string from the image; and determining whether the component to be inspected is a correct component by comparing the extracted character string with a character string to be printed on the component to be inspected.

2. The mounting-error inspecting method according to claim 1, wherein the component identifying information is information showing a mounting position on a substrate of the component to be replaced or replenished and design data or substrate inspection data for a component to be inspected is referred to specify a component to be inspected in the step of specifying a component to be inspected.

3. The mounting-error inspecting method according to claim 1, wherein the component identifying information is information showing the type of the component to be replaced or replenished and substrate design data or substrate inspection data for a component to be inspected is referred in accordance with the type of the component to specify a component to be inspected in the step of specifying a component to be inspected.

4. The mounting-error inspecting method according to claim 1, wherein the component identifying information is information for identifying a feeder to which the component to be replaced or replenished is supplied and mount data used in the component mounting step is referred in accordance with the feeder identifying information to specify a component to be inspected.

5. A mounting-error inspecting method wherein inspection same as the inspection for a substrate specified as a substrate corresponding to the substrate identifying information is executed for a predetermined number of substrates supplied after the specified substrate in the mounted component inspecting method of claim 1.

6. The mounting-error inspecting method according to claim 1, wherein when a determination result that a predetermined number of substrates or more are correct components among the substrates specified as components to be inspected is obtained, an inspection result that correct components are mounted on a substrate to be inspected is output.

7. A mounting-error inspecting method for inspecting whether a correct component is mounted on a component mounting substrate passing through a component mounting step, comprising:

setting component identifying information for identifying a component when processing of replacing or replenishing the component is executed in the component mounting step, obtaining the component identifying information set in the component mounting step;

specifying a component to be inspected in accordance with the component identifying information being executed in an inspecting step on whether a correct component is mounted for a predetermined number of substrates to be supplied after component identifying information is obtained, executing the inspection step;

obtaining the image of the component to be inspected;

extracting a character string from the image in the inspection;

comparing the extracted character string with a character string to be printed on the component to be inspected; and thereby determining whether the component to be inspected is a correct component are executed.

8. A substrate inspecting apparatus having a function of inspecting whether a correct component is mounted on a component mounting substrate prepared by and supplied from a component mounting machine, comprising:

an entering part for entering a character string to be printed on each component on a substrate to be inspected;

an information obtaining part for obtaining component identifying information for identifying a component replaced or replenished in the component mounting machine and substrate identifying information for identifying a specific substrate on which the replaced or replenished component is mounted;

a specifying part for specifying a substrate corresponding to the substrate identifying information among substrates to be supplied and specifying a component to be inspected in accordance with the component identifying information;

a determining part for executing processing of extracting a character string from the obtained image to be inspected and processing of comparing the extracted character string with the character string entered by the entering part and determining whether a correct component is mounted on the substrate in accordance with the comparison result; and an outputting part for outputting inspection result information including the determination result by the determining part.

9. The substrate inspecting apparatus according to claim 8, wherein the entering part enters component inspection data including the character string to be printed on each component on a substrate to be inspected.

10. The substrate inspecting apparatus according to claim 8, wherein the determining part determines that a correct component is mounted on a substrate to be inspected when a comparison result that the extracted character string is adapted for a character string corresponding to the component to be inspected is obtained for a predetermined number of components or more among a plurality of components specified as the components to be inspected.

11. A substrate inspecting apparatus having a function of inspecting whether a correct component is mounted on a component mounting substrate prepared by and supplied from a component mounting machine, comprising:

an entering part for entering a character string to be printed on each component on a substrate to be inspected;

an information obtaining part for receiving component identifying information for identifying a component replaced or replenished transmitted from the component mounting machine;

a specifying part for specifying a component to be inspected in accordance with the component identifying information;

a determining part for executing processing of obtaining the image of the component to be inspected on each substrate and extracting a character string from the image and processing of comparing the extracted character string with the character string entered by the entering part for a predetermined number of substrates supplied after receiving the component identifying information and determining whether a correct component is mounted on the substrate in accordance with the comparison result; and an outputting part for outputting inspection result information including the determination result by the determining part.

* * * * *